United States Patent [19]

Shanbrom

[11] 3,949,743

[45] Apr. 13, 1976

[54] MEDICATED VAPOR PRODUCTION METHOD AND APPARATUS

[75] Inventor: Edward Shanbrom, Santa Ana, Calif.

[73] Assignee: Schick Incorporated, Lancaster, Pa.

[22] Filed: Sept. 6, 1974

[21] Appl. No.: 503,860

Related U.S. Application Data

[63] Continuation of Ser. No. 342,820, March 19, 1973, abandoned.

[52] U.S. Cl. ............................ 128/173.1; 128/368
[51] Int. Cl.² ................. A61H 33/00; A61M 16/00
[58] Field of Search ............. 128/173.1, 173 R, 184, 128/140, 187, 192, 193, 195, 196, 197, 368, 205, 209

[56] References Cited
UNITED STATES PATENTS

| | | | |
|---|---|---|---|
| 2,622,593 | 12/1952 | Peirano ............................ | 128/173.2 |
| 2,788,784 | 4/1957 | Birch et al. ......................... | 128/201 |
| 3,334,627 | 8/1967 | Gorman ............................. | 128/208 |
| 3,490,452 | 1/1970 | Greenfield ......................... | 128/196 |
| 3,707,971 | 1/1973 | Yamamoto ......................... | 128/368 |

FOREIGN PATENTS OR APPLICATIONS

| | | | |
|---|---|---|---|
| 241,020 | 11/1964 | Austria ............................... | 128/368 |
| 649,263 | 11/1962 | Italy .................................... | 128/368 |
| 562,641 | 3/1957 | Italy .................................... | 128/173 |

Primary Examiner—Robert W. Michell
Assistant Examiner—Henry J. Recla
Attorney, Agent, or Firm—Lockwood, Dewey, Zickert & Alex

[57] ABSTRACT

Improved method and apparatus for the treatment of respiratory, skin, eye and related ailments and conditions wherein steam or a related vapor at a reduced temperature is admixed with particulate medicament and exposed to an afflicted area within a confined space.

9 Claims, 7 Drawing Figures

MEDICATED VAPOR PRODUCTION METHOD AND APPARATUS

This is a continuation of Ser. No. 342,820, filed Mar. 19, 1973, now abandoned.

BACKGROUND OF THE INVENTION

The present invention is directed to a method and apparatus for the production of an improved medicated vapor which is useful in the treatment of respiratory diseases and conditions, skin and eye diseases and conditions, and breath odors. In the preferred form of the invention, specially conditioned steam and a vaporized medicament or treating agent are combined in a new and novel manner to establish a highly useful and effective medication or treating agent for use in the treatment of a variety of respiratory, including mucous membrane, diseases and conditions in a simple, sterile, and effective manner, the resulting medication or treating agent further being capable of effectively masking undesirable respiratory odors commonly referred to as "bad breath" for an extended and satisfactory period of time.

In substance, the preferred form of the invention, as will be described hereinafter, involves the forming of a medicated or treating agent fog comprised of a steam generated water vapor carrier having injected there into and thoroughly admixed therewith a medicament or treating agent of various types and designed for treatment of various diseases and conditions, the injection and admixing of the vapor and medicament or treating agent being brought about under controlled conditions and being made available for use by inhalation or other appropriate modes in a substantially improved manner.

While the subject invention is fully adaptable for use in hospitals and the like, it is also adaptable for use in the home under conditions not requiring medical supervision. Various forms of generated steam vaporizers and cold water vapor mist generators, the latter known as nebulizers, have been used for many years and are currently being used in the treatment of respiratory congestion and the like both in the hospital and in the home. Steam vapor generators utilizing a discharge nozzle in the form of a relatively small size orifice directly associated with a medicament supply tube partially immersed in a liquid medicament whereby through negative pressure action the medicament is drawn upwardly through the supply tube into the steam jet constitute conventional equipment. A similar type of steam vaporizer differs only in that the ganerated steam is immediately passed through a chamber into direct contact with the medicament and the resulting vaporized mixture is discharged through a confined nozzle-like member for inhalation by the patient. In both of these types of widely used equipment, it has been found that the scope of use for various types of respiratory diseases and conditions is materially limited because a number of the most effective and desirable medicaments are temperature sensitive to an extent that undesirable modification or deterioration of the medicament will occur as a result of being subjected to the high temperature of the steam carrier regardless of the method under which the medicament is admixed with the steam. For example, derivatives and analogues of epinephrine, such as phenylephrine which is very effective in the treatment of nasal and sinus disorders as well as hay fever, will undergo chemical decomposition or undesirable change when subjected to high temperatures such as in the magnitude of 200°F. It has been found that the aforementioned common type of steam vaporizers will operate at a temperature of from 210° to 225°F. at the end of the discharge with the at which point the steam is either being admixed withthe medicament or has already been admixed with the same. Actually, discharge temperatures can reach as high as 240°F. depending upon the amount of pressure developed within the vaporizer. Adrenalin and its related compositions are also temperature sensitive in the manner aforementioned. Adrenalin and certain derivatives are widely used in connection with the treatment of asthma. Cortisone has been widely accepted as a treating agent for various skin conditions and eye problems and has more recently been found to provide beneficial effects in connection with lung diseases and related problems. Here again, cortisone is heat sensitive and cannot effectively be used in conventional types of steam vaporizers.

It is not uncommon at the present time for persons suffering from emphysema, for example, to make rather frequent trips to a hospital for treatment under supervision. The primary reasons for such supervised treatment is that it is important to maintain close control over the dosage of the medicament used, that it is important to guard against bacterial infection, and that the type of equipment available for such treatment is too expensive and complicated in operation for convenient home use.

Hand held and operated spray devices, either of the aerosol or aspirator type, which are available for private and independent use by persons suffering from various types of respiratory ailments, have not been found to be completely satisfactory even though in certain instances such devices are capable of dispensing a metered or properly measured dosage. Such sprays do not provide the requisite deep lung penetration for at least two reasons. First, it has been found that the average person cannot consistently and effectively coordinate deep lung inhalation with the manual operation of the spray device. Still further, by confining the discharge end of the spray device in the nostrils or mouth, the more immediate areas of the nostrils and mouth are possibly heavily treated preferentially to the more remote passages and particularly the deep lung portions. Thus, uniform treatment under metered dosage conditions is most difficult, if not impossible, to attain.

In more recent years it has been more popular to make use of cold water vapor nebulizers in the treatment of respiratory ailments. This type of apparatus is simpler in construction and operation than steam vaporizer apparatus. However, it has now been established that a number of undesirable effects result from the use of such cold water nebulizers. For example, the nebulizers provide an aseptic steam which includes bacteria, fungus, etc. already existing in the available water supply. Specifically, it has been found that cold steam may actually worsen asthma by reason of dispersing fungi in the lungs. Ultrasonic nebulization therapy should be used with caution because the water mist might cause a temporary deterioration in the mechanical lung function as well as a derangement in blood gas levels.

SUMMARY OF THE INVENTION

It is an object of the present invention to provide a new and improved medicated vapor production method capable of overcoming the disadvantages heretofore existing.

It is a further object of the invention to provide a new and improved form of apparatus capable of practicing the method of the invention.

Still a further object is to provide a method and apparatus capable of supplying a medicated vapor in the form of a fog including a specified and controlled dosage content of medicament uniformly dispersed throughout and in admixture with relatively low temperature vapor of steam-like consistency.

It is a further object to provide a method and apparatus capable of use in the treatment of one or more of respiratory disorders, mucous membrane disorders, eye disorders, skin disorders and breath odors.

Still a further object of the invention is to provide a method and apparatus capable of forming an admixture of medicament and steam under conditions maintaining the stability and efficacy of the medicament.

In accordance with the invention, steam or comparable substance is introduced into a confined patient treatment area at atmospheric or substantially atmospheric pressure and at reduced temperature. A medicament or treating agent, such as a breath odor masking agent, is introduced into the steam under conditions resulting in the formation of a substantially uniform fog and the resulting fog is applied to the area of the patient undergoing treatment either by mere exposure to such area or by inhalation on the part of the patient. As a result of the practice of the invention, the medicament used is not subjected to a deleterious environment and is at least substantially uniformly dispersed throughout the steam atmosphere to provide a stable and measureably controlled dosage. The resulting medicated fog may be used for the treatment of numerous respiratory and skin disorders, is sterile, readily inhaled in a uniform manner, and can be constituted to treat eye disorders as well as undesirable breath conditions.

DESCRIPTION OF THE DRAWINGS

The present invention is set forth with particularity in the appended claims. The invention, together with the objects and advantages thereof, may best be understood by reference to the following description taken in connection with the accompanying drawings, in the several figures of which like reference numerals identify like elements, and in which:

DESCRIPTION OF THE PREFERRED EMBODIMENT

In the accompanying drawings, the invention is shown as incorporated in a portable steam generating unit 10 which is simple and sturdy in construction, economical in manufacture and available for convenient portable home use. The unit 10 constitutes a preferred form of the apparatus of the subject invention, but it is apparent that different forms of apparatus may be used in carrying out the method of the invention.

Figure 1:
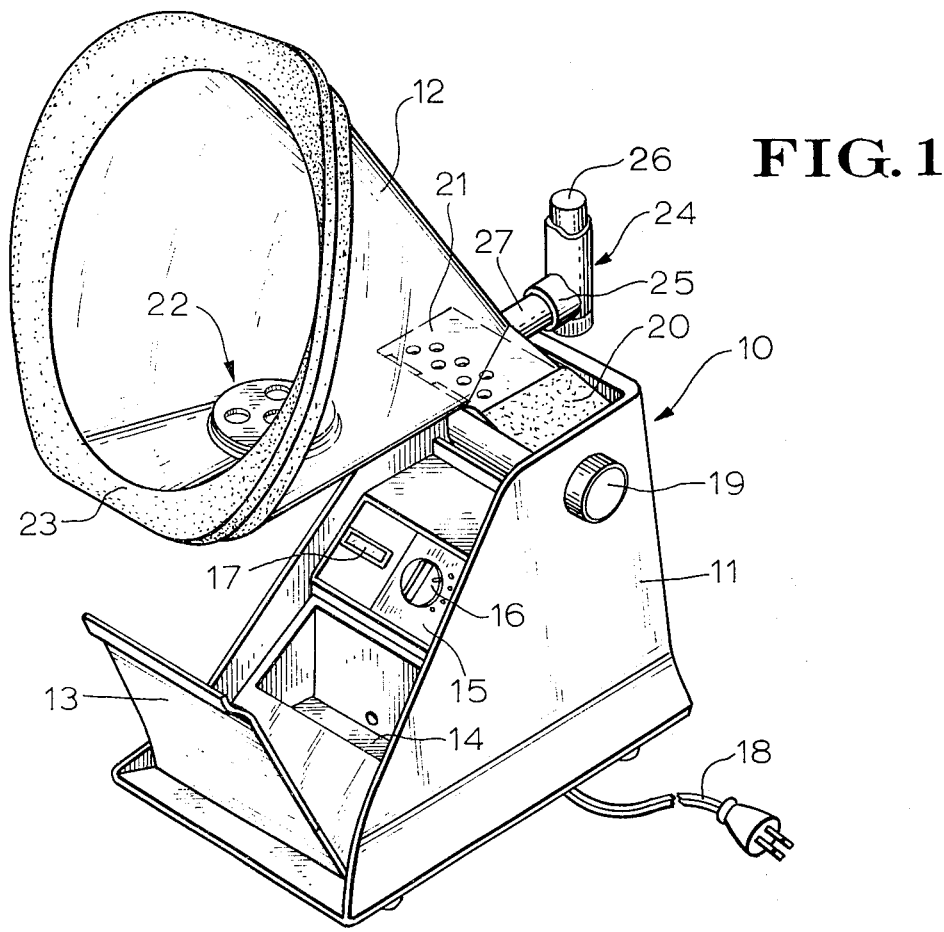
FIG. 1 is a perspective view of a preferred form of apparatus constructed in accordance with the invention.

Referring to FIG. 1, the unit 10 comprises a base housing 11 of generally trapezoidal cross section to the top of which is pivotally mounted a breathing hood 12. The base housing 11 has a hinged cover plate 13 on its inclined front face which when opened exposes a water reservoir 14. A control panel 15 is contained on the inclined face immediately above the reservoir and includes a selector switch 16 and a pilot lamp 17. A power line cord 18 is provided for supplying electrical power to the appliance.

The breathing hood 12 is pivotally mounted by means of a shaft 42 (see FIG. 3) extending between opposite sides of the housing, and is secured in a selected tilted position by the user by operation of a clamping knob 19 which is threaded onto one end of the shaft. Upon tightening of the knob 19 against the side of the housing, the breathing hood is clamped in a selected tilted position. The base neck of the hood 12 provides a relatively restricted passageway 20 of generally rectangular cross section communicating with the housing 11 and the inside area thereof, such passageway terminating at a perforated steam columnating plate 21. This plate, as will be explained in detail hereinafter, is instrumental in assisting introduction of steam into the main portion of the hood in a uniformly dispersed and temperature reduced condition. If desired, an adjustable air inlet 22 may be provided in the bottom surface of the hood 12 for the purpose of allowing a controlled amount of outside air to enter the hood and mix with the steam and medicament within the hood. A soft gasket-type cover 23 is provided around the opened rim of the hood to establish a seal with the face of the user as best illustrated in FIG. 2.

Figure 3:
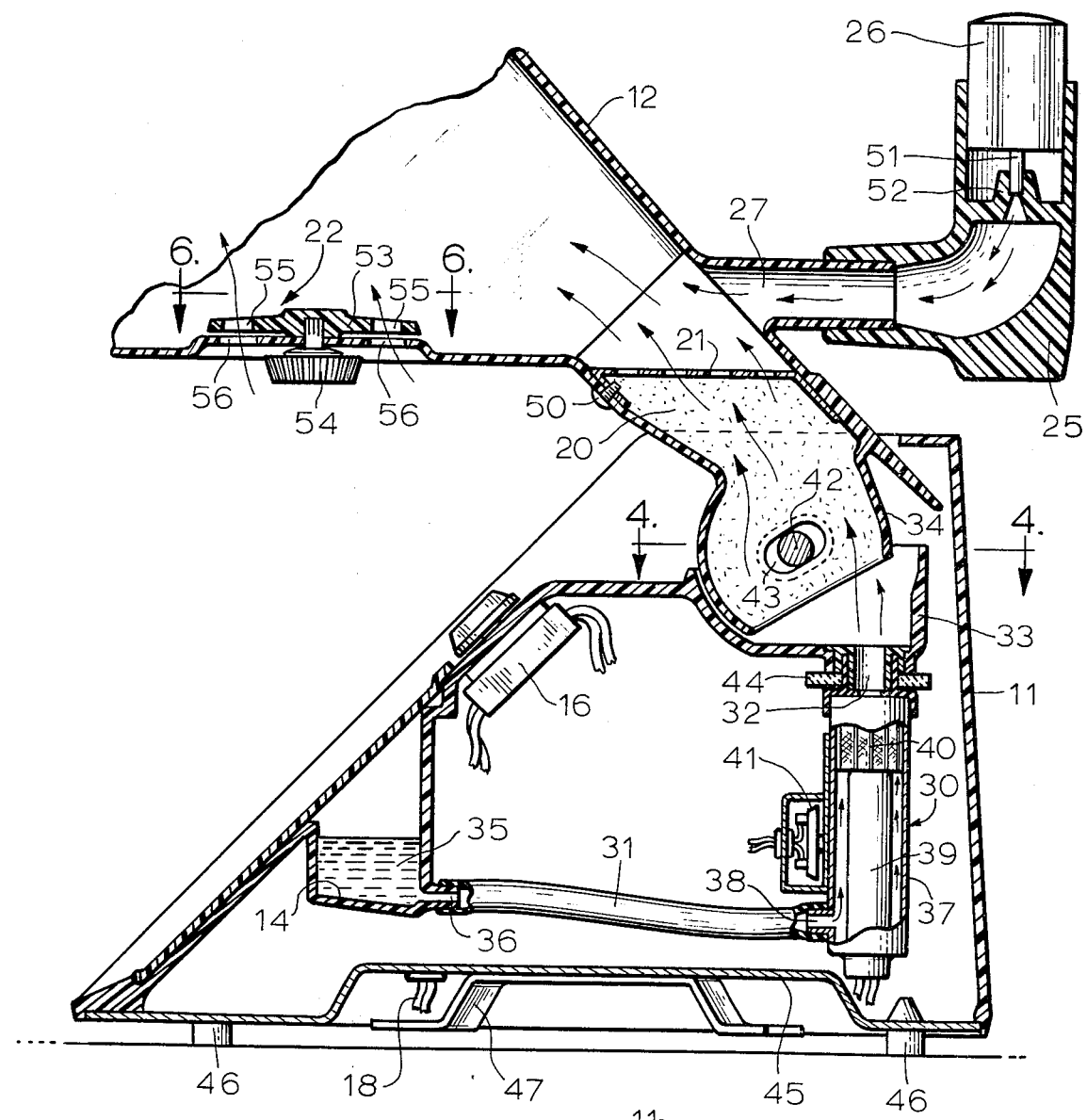
FIG. 3 is a cross sectional view of a portion of the apparatus.

The apparatus of FIG. 1 further includes a user-actuated medicament supply assembly 24 which upon actuation by the user injects a fine spray of medicament into the steam vapor in the hood as the vapor is entering the hood in the reduced cross sectional area of the hood immediately adjacent the perforated plate 21. The medicament supply assembly 24 includes an L shaped housing 25 having a vertical portion adapted to receive a medicament container 26, such as a known type of aerosol container or an aspirating type of container, as well as a horizontal portion which is mounted on a supporting tube 27 suitably fixed to the adjacent wall of the hood and in communication with the interior of the hood as best illustrated in FIG. 3. This assembly is preferably capable of disassembly for cleaning purposes. The medicament injector assembly 24 is preferably located relative to the hood to inject the medicament in a measured dosage manner into the steam substantially concurrently with the entry of the steam into the hood 12.

Figure 2:
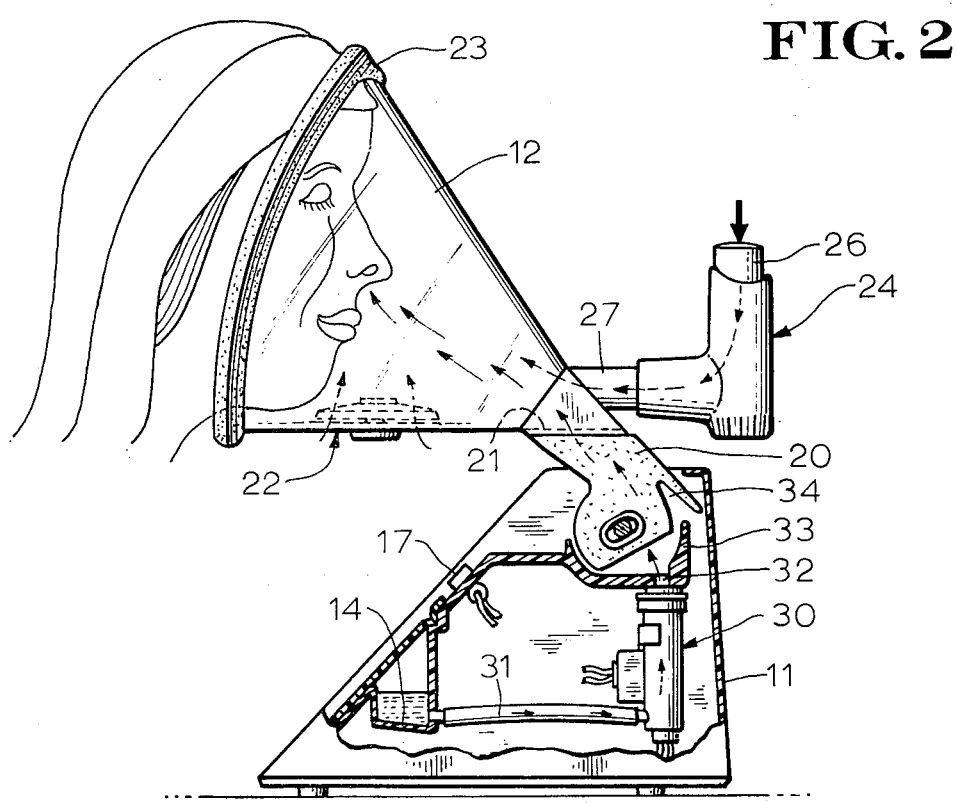
FIG. 2 is a side elevational view, partly in cross section, illustrating the apparatus.

FIG. 2 illustrates in greater detail the base of the housing 11 as including a steam generator 30. Electrical power is supplied to the generator and the resulting steam exits through an aperture 32 directly into passageway 20 of the hood. The housing 11 is provided with a baffle 33 extending upwardly immediately adjacent the aperture 32 which cooperates with an overlapping baffle 34 forming a part of the base portion of the hood 12. As a result of this cooperation, regardless of the inclination of the hood, a substantially vapor-tight seal is established adjacent the pivot point of the hood.

Figure 4:
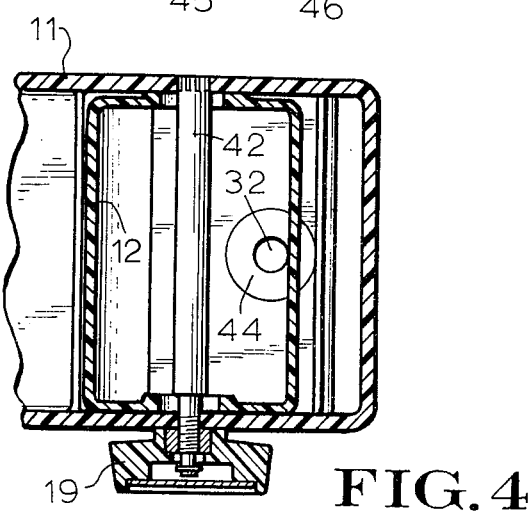
FIG. 4 is a cross-sectional view of the apparatus taken along lines 4—4 of FIG. 3.

FIG. 3 best illustrates the functioning of the steam generating portion of the apparatus. Water reservoir 14 is illustrated as being partially filled with water or other suitable vapor forming liquid 35. Outlet port 36 extends from the reservoir and is received in hose 31. In turn, hose 31 is connected to the generator 30 by port 38 forming a part of the generator housing 37. Such housing is preferably of steel or a similar heat-resistant material. An elongated tubular electric heating element 39 is disposed within the housing 37 for the purpose of heating the water received from the reservoir 14 as the water seeks its own level within the housing 37. Heating element 39 may be of conventional design and construction such as consisting of a pair of resistance elements adapted to be powered singly or in pair by an applied AC line voltage. The heating element extends up through the bottom of housing 37 and along approximately two-thirds of the length of the housing. A splash shield 40 consisting of a wad of steel mesh is provided above the heating element near the top of housing 37 to prevent the water from splashing into passageway 20. An electrical over-heat cut-out switch 41 is positioned adjacent the sidewall of housing 37 for the purpose of interrupting current flow to the heating element should the element over-heat such as when the water supply becomes exhausted. As shown in FIG. 4, a gasket 44 is mounted around the aperture 32 to further assist in maintaining a steam-tight fit between the housing 11 and the steam generator 30. As additionally shown in FIG. 4, the shaft 42 has one end fixed in one sidewall of the housing and the other end threadedly receives the locking knob 19.

Figure 5:
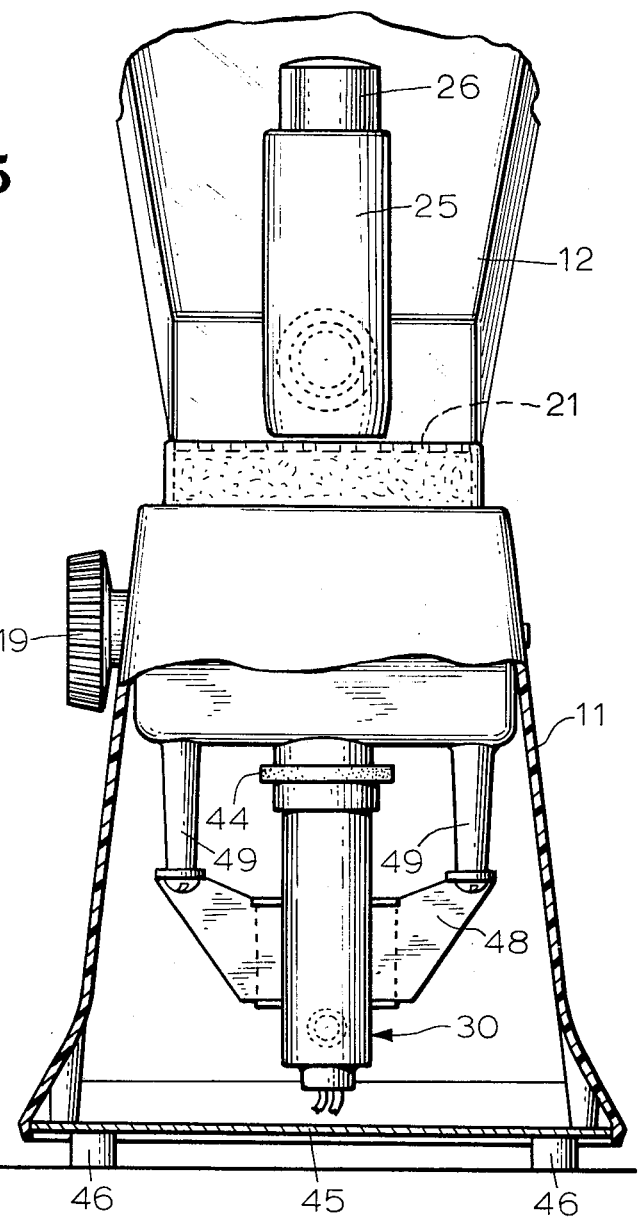
FIG. 5 is a rear elevational view, partly fragmentary, of the apparatus.

FIG. 3 illustrates the housing 11 as being closed at the bottom by a cover plate 45 which is fastened to the housing in an appropriate manner. A plurality of rubber mounting feet 46 support the entire housing in spaced relation to a supporting surface. The bottom plate 45 is centrally recessed and receives a wing-shaped bracket 47 about which the power cord 18 may be coiled for storage. In FIG. 5 the steam generator 30 is illustrated as supported by a bracket 48 in turn fastened to a pair of supporting studs 49 molded into the housing 11.

FIG. 3 illustrates the apertured plate 21 as being fixed in the neck of the hood 12 by a suitable fastener 50. The medicament supplying unit 24 as illustrated in FIG. 3 includes the known type of aerosol container 26 provided with a nozzle 51 which is received within a centrally apertured support 52 forming a part of the housing 25. Upon depressing the aerosol container, the nozzle 51 will recede into the container and stored medicament will be sprayed through the central aperture in the support 52, through the bottom portion of the housing 25, and into the hood 12 through the tube 27. The construction of the aerosol container 26, nozzle 51 and the manner in which the unit is operated as illustrated in FIG. 3 is well known and does not constitute a part of this invention.

Figure 6:
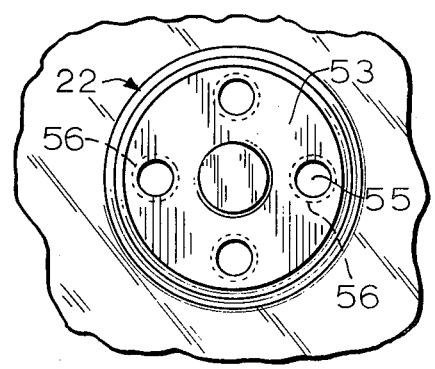
FIG. 6 is a fragmentary elevational view taken along lines 6—6 of FIG. 3.

Referring to FIGS. 3 and 6, the air mixing valve assembly 22 forming a part of the hood 12 includes a rotatable disc 53 fixed to a knob 54 and provided with a plurality of apertures 55. The bottom wall portion of the hood 12 includes a recessed area which is formed with a plurality of apertures 56. The knob 54 extends outwardly through the recessed area and upon rotation of the same the inner disc 53 may be rotated so that selective alignment of apertures 55 and 56 may be accomplished. Such apertures are so spaced that the interior of the hood 12 may be completely sealed off from the introduction of any outside air.

Figure 7:
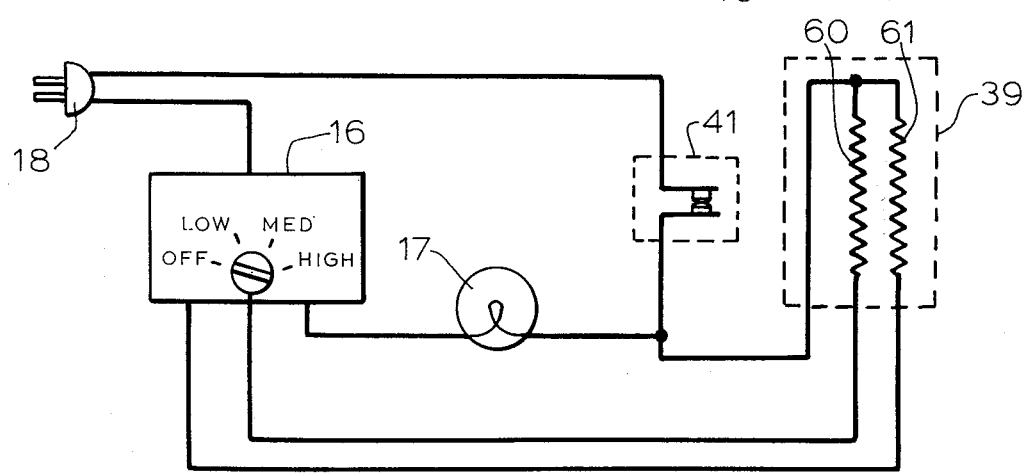
FIG. 7 is a schematic diagram of the electrical circuit of the apparatus.

The electrical circuit of the unit is schematically shown in FIG. 7. Basically, one side of the AC line is connected to switch 16, which comprises a four position rotary switch adapted to connect various combinations of heating elements to the AC line in the low, medium and high operating conditions for variation in the degree of steam generation. The other side of the AC line is connected through the over-heat cut-off switch 41 to the common terminal of the electric heating element 39. Heating element 39 actually comprises two electrical resistance elements, a lower resistance element 61 and a higher resistance element 62. In practice, the low resistance element may be an 80 watt unit and the high resistance element a 50 watt unit. At low temperature operation, the higher resistance element 62 is connected across the AC line by the switch 16 to achieve the lowest heat output. In the medium temperature operation the lower resistance element 61 is connected across the AC line to obtain the 80 watt output. In the high heat condition the two heating elements are connected in parallel across the line for the greatest possible heat output, in this case 130 watts. Whenever one or both of the resistance elements is energized, switch 16 also connects indicator lamp 17 to the AC line to indicate to the user that steam is being generated.

FIGS. 2 and 3 best illustrate operation of the apparatus of the invention. As indicated in FIG. 2, after initial actuation of the unit and adequate preliminary steam generation so that the hood 12 is substantially filled with steam, the user's face is applied against the cushioning and sealing gasket element 23 so as to expose the respiratory system or other areas to be treated to the steam environment. The user then depresses the medicament container 26 downwardly in the direction of the arrow in FIG. 2 to the fullest extent as controlled by total movement available in the nozzle 51 in accordance with conventional operation of such containers. Medicament is sprayed in a measured quantity from the container through the aligned passageways into the hood and, as illustrated, slightly obliquely to the normal flow of steam or at a slight angle to such normal flow. The angle at which the medicament is injected into the steam is preferably such that the direction of medicament flow is substantially, if not completely, in the same direction as the flow of the steam. This arrangement assures complete diffusion and intermingling of the medicament with the water vapor particles so as to establish uniformity in the ultimate admixture. Among other things, bearing in mind that in the treatment of serious ailments and diseases in which controlled dosage is essential, by complying with this preferred procedure the medicament is fully admixed with the steam without loss of medicament by reason of deposit of the same along the interior surfaces of the hood.

The medicament is injected into the steam environment in a very fine spray with the medicament particles typically and preferably not exceeding approximately two microns. Again, this preferential practice of the subject invention is of real significance in connection with the treatment of serious diseases and conditions requiring carefully controlled dosage. Such a requirement is not of particular significance in connection with beauty treatment of the skin, treatment of the common cold using menthol or the like, or the freshening of breath using a mint spray or the like.

Another preferred aspect of the invention resides in the fact that the area of the portion of the hood into which the medicament is injected is of restricted size relative to the remaining portion of the hood, and still further, the location of medicament injection relative to the user's face is preferably remote. The area of the portion of the hood 12 immediately above the apertured plate 21 into which area the medicament is injected is of substantially reduced cross section as compared to the remaining expanding cross section of the hood. In this area of reduced cross section the steam is relatively dense and the medicament, which is injected in the quantity of a prescribed dosage, becomes thoroughly admixed with the steam thereby providing uniformity in dispersion of the resultant mixture as such mixture expands into the increased cross sectional area of the hood. This feature is of significance from the standpoint that many medicaments used for the treatment of rather serious diseases and conditions must be applied in measured dosages and the beneficial effects to be obtained from each dosage necessitates full and uniform utilization of the same. The method and apparatus of the subject invention is directed to this end result and very effectively obtains the same.

Where temperature sensitive medicaments are used, it is essential that the temperature of the generated steam at the point of medicament injection be sufficiently low to preclude undesirable modification or destruction of the medicament. As can be readily appreciated from a consideration of the description of the operation of the apparatus, the generated steam rises from the generator 30 through a series of passageways of increasing cross sectional area thereby assuring that such steam is at or about atmospheric pressure upon movement into the area immediately above the apertured plate 21. In the absence of any super-atmospheric pressure conditions, the initial temperature of the steam cannot be maintained and will drop appreciably as a result of heat exchange relationship with the adjacent parts of the apparatus as well as from mere volumetric expansion alone. Thus, for example, as mentioned hereinabove in connection with known types of steam vaporizers having discharge nozzle portions of very restricted cross sectional area, steam temperatures at or well above the boiling point of water are completely eliminated. Actually, it has been found by appropriate testing that the temperature of the steam in the area above the aperture plate 21 of the subject apparatus falls within the approximate range of 120° to 140°F. At such temperatures there is no possibility of any degradation of the well known medicaments such as listed hereinabove. As illustrative of this significant advantage, epinephrine decomposes at 212°F. and cortisone decomposes at 217° to 224°F.

The aperture plate 21 of the hood 12 is not essential to the practice of the invention but constitutes a preferred element. The presence of the apertures in the plate 21 provides a columnating effect to the rising steam so as to minimize if not prevent the existence of any tubulence in the steam flow, thus improving the dispersing of the medicament uniformly throughout the steam atmosphere. Still further, the combination of the plate 21 and the rising columns of steam prevents any undesirable loss of medicament by injection of any portion of the same downwardly rather than directly into the upward steam flow. The relatively low temperature of the steam in the area of medicament injection further minimizes the possibility of condensation resulting from intermingling of vapor-like substances each at dramatically different temperatures. The resulting uniformly dispersed admixture in the hood, which is in the form of a measured dose, provides the advantage of continued inhalation of a quantity of medicament within the safety limit prescribed by the patient. In other words, steam itself is well known and well accepted as being particulary helpful as a hydration agent in relieving respiratory ailments. Continued inhalation of additional quantities of steam will not have any adverse effect but, on the other hand, continued inhalation of additional quantities of medicament beyond the prescribed dosage can have harmful effects. In using the method and apparatus of the invention, the possibility of over-dosage of medicament is completely avoided and the probability of obtaining the full benefits of the prescribed dosage is greatly increased. Only the single prescribed dosage of medicament is made available to the patient whereas additional quantities of steam are supplied. Thus, upon continued inhalation while the patient is inhaling additional quantities of steam, ultimately the full dosage of medicament, and no more, will be inhaled.

Another significant advantage obtained from a practice of the invention is the elimination of exposure of the areas being treated to bacteria and fungi. The water vapor is completely free of bacteria as a result of steam generation, the medicament is packaged under antiseptic conditions, and the resulting fog is completely free of infectious and irritating materials. The outside air intake unit 22 of the hood 12 may be completely eliminated from the apparatus if desired. It might well be provided only for use in the treatment of conditions where close control over antiseptic conditions is not absolutely necessary. At any rate, if the venting arrangement is used, only controlled and relatively small amounts of outside air will be infused into the system.

The subject invention eliminates the necessity of the patient exercising careful control over the timing of inhalation with the dispensing of medicament. It has been found that it is exceedingly difficult for the average person to precisely time deep breathing with manipulation of a medicament spray. With use of the present invention the patient need merely breath in the normal manner. Furthermore, as can be appreciated in connection with respiratory ailments, repeated breathing of a medicated fog of the type supplied by the present invention will result in continued improvement of the capacity to fill the lungs. Thus, in the instance where mucous membrane is considerably swollen, repeated breathing of the medicated fog will result in shrinkage and reduction of the swollen membranes thereby ultimately providing complete relief from the condition. Where merely a spray is used, bearing in mind that the dosage must be carefully controlled, there is little opportunity for repeated breathing so as to obtain full advantage of the prescribed dosage.

As mentioned hereinabove, the eyes may be treated using the method and apparatus of the invention. Such treatment may extend to elimination of ordinary irritation as well as chronic inflammatory conditions such as conjunctivitis, eyelid infections, and irritation due to contact lenses and smog. The nasal passages may be readily treated in connection with adverse effects due to the common cold, allergic rhinitis and hay fever. The sinuses may be treated for chronic and allergic sinusitis. The ears may be treated in connection with chronic ear infections as well as aerotitis secondary to air flights and scuba diving. The throat may be treated in connection with irritation due to smoking. Laryngitis and croup may be effectively treated. In the lungs, asthma as well as emphysema may be readily treated. Acne and inflammatory diseases of the skin including dermatitis may be readily treated.

In connection with the masking of breath odors, it must be borne in mind that the lungs are to a substantial extent a basic source of such odors. During normal breathing there is at least 20 to 30% residual air retained in the lungs which picks up odors from the gastro-intestinal tract. By a practice of the present invention suitable odor masking materials, such as mint, may be inhaled into the lungs to provide advantageous effects at one of the primary sources of breath odors.

While a particular embodiment of the invention has been shown and described, it will be obvious to those skilled in the art that certain changes and modifications may be made without departing from the basic concept of the subject invention as set forth in the claims appended hereto.

I claim:

1. Apparatus for applying a particulate medicament of a type subject to decomposition when heated above a predetermined temperature to an afflicted area comprising, in combination:
   steam generating means having a discharge orifice for generating a vapor mist whereby the initial temperature of said generated vapor mist at said orifice is above said predetermined temperature;
   conduit means defining a flow path for said vapor mist from said discharge orifice to the afflicted area whereby the temperature of said vapor mist progressively decreases as said mist progresses along said flow path and eventually falls below said predetermined temperature at a first predetermined location along said flow path; and
   medicament introducing means for injecting the medicament in particulate form into said flow path at a second predetermined location along said flow path substantially downstream from said first predetermined location whereby the medicament intermingles with said vapor mist after the temperature of said mist has fallen below said predetermined temperature to reduce the likelihood of temperature-induced decomposition of the medicament.

2. The apparatus of claim 1 wherein said medicament introducing means introduce the medicament into said conduit means at an angle substantially coincident with the flow of said steam mist.

3. The apparatus of claim 1 wherein said conduit means include a hood portion defining a portion of said flow path having a progressively increasing cross-sectional area, and a neck portion establishing communication between said hood portion and said steam generating means, and wherein the medicament is introduced in substantial coincidence with the flow of said vapor mist through said hood portion so as to uniformly intermix with said vapor mist as said mist expands therein.

4. The apparatus of claim 1 wherein said medicament introducing means include an atomizer for forming said medicament into a spray of fine particles.

5. The apparatus of claim 4 wherein said medicament introducing means include means for limiting the quantity of medicament injected to obtain a predetermined dosage.

6. Apparatus for applying a particulate medicament subject to thermal decomposition when heated above a predetermined temperature to an afflicted area comprising, in combination:
   steam generating means including a discharge orifice for generating a vapor mist whereby the initial temperature of said generated vapor mist at said discharge orifice is above said predetermined temperature;
   conduit means defining a flow path for said vapor mist from said discharge orifice to the afflicted area, a portion of said conduit means downstream of said orifice comprising a hood of progressively increasing cross-sectional area opening onto said afflicted area, the temperature of said vapor mist progressively decreasing as said vapor mist proceeds through said hood and falling below said predetermined temperature at a predetermined location therein; and
   medicament injection means for injecting the medicament as a spray of fine particles into said flow path at a location substantially downstream of said predetermined location and in a direction at least partially coincident with the direction of flow of said vapor mist through said hood whereby said medicament is uniformly intermixed with said vapor mist within said hood after the temperature of said mist has fallen below said predetermined temperature to avoid thermal decomposition of the medicament.

7. The apparatus of claim 6 wherein said medicament injection means include an atomizer having means for limiting the quantity of medicament injected to obtain a predetermined dosage.

8. The method of treating an afflicted area with a medicament subject to thermal decomposition when heated above a predetermined temperature comprising the steps of:
   forming a vapor mist;
   directing said vapor mist through a discharge orifice and along a conduit defining a flow path whereby said vapor mist has an initial temperature at the orifice sufficiently high to subject the medicament to thermal decomposition, and whereby the temperature of said mist progressively decreases as said mist flows along said flow path and falls below said predetermined temperature at a predetermined location along said flow path;
   injecting the medicament in particulate form into said flow path at a location substantially downstream of said predetermined location to avoid thermal decomposition of said medicament;
   maintaining the resulting admixture in a confined space; and
   exposing the afflicted area to the the resulting admixture within said confined space.

9. The method of claim 8 wherein said medicament is injected into said vapor mist in a direction substantially coincident with the direction of flow of said mist through said conduit.

* * * * *